United States Patent
Makoui et al.

[11] Patent Number: 6,127,595
[45] Date of Patent: Oct. 3, 2000

[54] COVER SHEET LAMINATION FOR ABSORBENT ARTICLE AND LOW TEMPERATURE LAMINATION PROCESS

[75] Inventors: Kambiz Bayat Makoui; Bernard Michael Koltisko, both of Allentown; Thomas S. Jones, Wescosville, all of Pa.

[73] Assignee: Air Products and Chemicals, Inc., Allentown, Pa.

[21] Appl. No.: 09/064,702

[22] Filed: Apr. 22, 1998

[51] Int. Cl.[7] ................................................. A61F 13/15
[52] U.S. Cl. .................... 604/367; 604/358; 604/365; 604/366; 604/368; 604/385.01; 604/387
[58] Field of Search ...................... 604/387, 368, 604/389, 367, 365, 366, 358, 385.01; 521/148; 523/111; 524/502; 162/112

[56] References Cited

U.S. PATENT DOCUMENTS

| | | | |
|---|---|---|---|
| H1511 | 12/1995 | Chappell et al. | 604/383 |
| Re. 26,151 | 1/1967 | Duncan et al. | 604/387 |
| 3,180,335 | 4/1965 | Duncan et al. | 604/385.1 |
| 4,405,310 | 9/1983 | Karami | 604/383 |
| 4,507,173 | 3/1985 | Klowak et al. | 162/112 |
| 4,753,648 | 6/1988 | Jackson | 604/389 |
| 4,798,604 | 1/1989 | Carter | 604/383 |
| 4,860,737 | 8/1989 | Lang . | |
| 4,861,652 | 8/1989 | Lippert et al. | 428/284 |
| 5,260,345 | 11/1993 | DesMarais et al. | 521/148 |
| 5,342,861 | 8/1994 | Raykovitz | 523/111 |
| 5,401,268 | 3/1995 | Rodier | 604/385.1 |
| 5,533,991 | 7/1996 | Kirby et al. . | |
| 5,562,646 | 10/1996 | Goldman et al. | 604/368 |
| 5,599,339 | 2/1997 | Horney | 604/387 |
| 5,788,684 | 8/1998 | Abuto et al. | 604/368 |
| 5,885,266 | 3/1999 | Chihani et al. . | |
| 5,900,451 | 5/1999 | Krishnan et al. | 524/502 |
| 5,972,505 | 10/1999 | Phillips et al. | 428/397 |

*Primary Examiner*—John G. Weiss
*Assistant Examiner*—Miley Craig Peppers, III
*Attorney, Agent, or Firm*—Russell L. Brewer

[57] ABSTRACT

This invention relates to an improvement in a disposable absorbent article such as a sanitary napkin, etc. having a liquid permeable cover sheet or cover sheet, optionally a distribution or transfer layer, an absorbent core and a liquid-impermeable backsheet. The improvement in the disposable absorbent article resides in an improved bond for generally continuous contact between the cover sheet and the transfer layer or absorbent core. Adhesion is effected by applying an adhesive binder to the top sheet with a print roller.

23 Claims, 4 Drawing Sheets

ABSORBENT PAD SCHEMATIC

Gravure Cylinder (Diamond Pattern)

Dimensions: Line Width 15 microns
Line Depth 35 microns
Diamond Long Axis 1000 microns
Diamond Short Axis 500 microns
Area Coverage 48 %

COVER SHEET LAMINATION FOR ABSORBENT ARTICLE AND LOW TEMPERATURE LAMINATION PROCESS

CROSS-REFERENCE TO RELATED APPLICATIONS

Not applicable.

STATEMENT REGARDING FEDERALLY SPONSORED RESEARCH OR DEVELOPMENT

Not applicable.

TECHNICAL FIELD

This invention relates to a process for the low temperature lamination of a perforated body side cover sheet to a distribution layer or absorbent core in the formation of disposable absorbent products and to the resultant product.

BACKGROUND OF THE INVENTION

Disposable absorbent articles, which include sanitary napkins, catamenial pads, panty liners and the like, are designed to absorb the discharge of body fluids such as urine and blood from a wearer. These articles typically are multi-layered in construction and are comprised of a liquid-permeable cover sheet having one side designed for placement in contact with the wearer, an absorbent core for effecting storage of the discharged body fluids and a liquid impervious backsheet for retaining the stored fluids within the disposable absorbent article. In early disposable articles, the liquid-permeable cover was affixed to the absorbent core for permitting rapid transfer of body fluids down into the absorbent. In more recent years it has been common to include a transfer or distribution layer between the underside of the cover sheet and the absorbent core to facilitate transfer of fluids. The transfer sheet or distribution layer is highly porous and has wicking capability which essentially pulls body fluids through the cover sheet with direction toward the absorbent core.

The attachment of the cover sheet to the transfer layer or absorbent core throughout its surface is a necessary practice to insure that good fluid transfer takes place. Currently, commercial manufacturers of the absorbent articles employ hot melt adhesives and/or heated embossing rolls to attach the cover sheet to the distribution layer or absorbent core of the absorbent product to each other. These are applied to the sides of the absorbent core typically in a hairline patten. A problem with hot melt adhesives is that they can plug the apertures in the cover sheet. Another problem associated with the employment of hot melt adhesives is that additional equipment is required, e.g., an applicator which melts the adhesive and a spray assembly for each converting machine. The latter requires constant cleaning and dealing with the plugged nozzles. A problem with heated embossing rolls for attaching the cover sheet to the transfer layer is that both temperature and pressure control must be carefully monitored to avoid distortion and or melting of the cover sheet.

Another mechanism for attaching cover sheets formed from carded webs is the use of thermoplastic bicomponent fibers. These fibers melt at elevated temperature and fuse with the distribution layer or absorbent core. As with melt adhesives, the use of bicomponent fibers requires close temperature control to prevent plugging of pores, distortion, etc.

The application of self sealable binders, such as a pressure sensitive adhesive, applied to an absorbent core can promote some bonding between the cover sheet and the absorbent core at room temperature. However, making a commercial air-laid roll with this type of binder is very difficult since the binder tends to block and bond the entire web when the roll is wound onto large drums for storage. The only way to prevent this problem is to add a release liner between the plies which adds to the cost.

The following patents are representative of multi-layer constructed disposable absorbent products suited for the applications addressed.

U.S. Pat. No. 5,401,267 discloses an absorbent article having enhanced wicking capacity. The absorbent article is comprised of a liquid-permeable cover, a liquid-impermeable baffle, and an absorbent core disposed between the liquid-permeable cover and the liquid-impermeable baffle. The cover sheet is comprised of a perforated polyethylene film for permitting rapid transfer of fluid to the absorbent core. Disposed between the cover sheet is a distribution or transfer layer which has a lower wicking capacity than the cover sheet and is formed of a hydrophilic material having a large pore structure and wet and dry resiliency to ensure comfort and protection. Coform and air-laid fabric are two materials that are used as the distribution layer.

U.S. Pat. No. 5,533,991 discloses absorbent articles for the applications described which comprise a cover sheet, an absorbent core and a liquid-impermeable baffle. The patentees disclose the use of one or more distribution or transfer layers between the cover sheet and the absorbent core, such layers assisting in keeping the cover dry by directing body fluids downwardly and away from the cover sheet and also to move the body fluids outward in the x and y directions so as to facilitate rapid fluid intake by the absorbent core. The cover sheet is described as including bonded-carded webs and plastic films having a plurality of apertures therein which have a thickness of less than 2 mm, generally between 0.05 and 2 mm. A second material (transfer layer) which is in contact with the cover sheet is provided to distribute fluids from the cover sheet to the absorbent core and these second materials are liquid-permeable nonwoven webs formed from a variety of materials such as polyesters, polyvinyl acetate, cellulose acetate, viscose and so forth. A variety of methods are used to bond the second material to the first material and these include mechanical attachment, adhesives, an ultrasonic bond, thermal bonds and pressure bonds.

H1511 discloses absorbent articles, especially sanitary napkins, containing flow regulators or distribution layers, between the cover sheet and the absorbent core. The patentees report that the absorbent article includes a fluid-pervious cover sheet, a fluid-impervious backsheet joined to the cover sheet and an absorbent core positioned between the cover sheet and the backsheet. The flow regulator is positioned between the cover sheet and the absorbent core and enhances the movement of fluid in the longitudinal direction while controlling movement of fluid in the transverse and Z directions. It is comprised of a plurality of fibers having external capillary channels. The cover sheet is described as an apertured film having a plurality of perforations, e.g., perforated polyethylene. The backsheet is described as a polyethylene film which is impervious to liquids. The absorbent core is described as comprised of common wood pulp sometimes referred to as "air felt" incorporating chemically stiffened and crosslinked cellulosic fibers, peat moss, tissue, etc. To enhance transfer of the fluids through the sanitary napkin the patentees indicate it's important to keep the layers in close or otherwise intimate contact and the contact can be achieved by means of adhesives, ultrasonics and so forth. Adhesives include latex adhesives and hot melt adhesives and may be applied in an open-patterned network of filaments.

U.S. Pat. No. 4,405,310 discloses sanitary napkins incorporating at least two absorbent pads with the lower absorbent pad being secured to the upper pad by means of an adhesive.

U.S. Pat. No. 4,861,652 discloses diapers incorporating a body cover in combination with an absorbent core and liquid-impermeable backsheet. The multi-layered construction of the diaper is held with each layer bonded to one another by thermal or sonic bonds or through the use of adhesives such as hot melt pressure-sensitive adhesives.

U.S. Pat. No. 4,798,604 discloses a water permeable, apertured, contoured polymeric film formed from an elastomer which is suited as a cover for absorbent articles such as sanitary napkins and the like. Two conventional procedures are used in the construction; one being the conventional route of disposing an absorbent material between a liquid-pervious body facing layer (cover sheet) and the fluid-impermeable backing layer (backsheet) and bonding the facing layer and fluid impermeable backing layer at their edges by means of heat sealing thereby enclosing the absorbent material. An alternate method involves bonding the body facing layer to the fluid-impermeable backing layer by means of a hot melt or pressure-sensitive adhesive.

BRIEF SUMMARY OF THE INVENTION

This invention relates to an improvement in a disposable absorbent article such as a sanitary napkin, diapers, etc. having multi-layer construction. The disposable absorbent article is comprised of a liquid permeable cover sheet or cover sheet having a wearer contact side and an underside, optionally a distribution or transfer layer, at least one absorbent core and a liquid-impermeable backsheet. The disposable absorbent article is constructed such that the absorbent core is disposed between the cover sheet and the backsheet and the distribution layer is disposed between the underside of the cover sheet and the absorbent core. The improvement in the disposable absorbent article resides in an improved bond for providing generally continuous contact between the cover sheet and the distribution layer or absorbent core and is comprised of the following:

said liquid-pervious cover sheet having said underside coated with a thermoplastic adhesive binder obtained by emulsion polymerization, said thermoplastic adhesive binder applied via a print roller such as a gravure cylinder to its underside;

said distribution layer or absorbent core each formed from a nonwoven web comprised of randomly distributed fibers, the fibers therein bonded with a thermoplastic adhesive binder obtained by emulsion polymerization, said thermoplastic adhesive binder employed in forming said distribution layer or absorbent core being adhesively compatible with said thermoplastic adhesive binder on said cover sheet; and, said underside of said liquid-pervious cover sheet coated with an adhesive binder and bonded to the surface of the adhesively coated distribution layer or adhesively coated absorbent core.

This invention also relates to an improvement in a process for producing a disposable absorbent article such as a sanitary napkin, etc. having multi-layer construction. The disposable absorbent article is comprised of a liquid permeable cover sheet or cover sheet having a wearer contact side and an underside, a distribution or transfer layer, at least one air-laid nonwoven absorbent core and a liquid-impermeable backsheet. The disposable absorbent article is constructed such that the absorbent core is disposed between the cover sheet and the back sheet and the distribution layer is disposed between the underside of the cover sheet and the absorbent core. The improvement in the process for forming the disposable absorbent article resides in providing an improved bond for effecting generally continuous contact between the cover sheet and transfer layer or absorbent core and comprises:

coating the underside of the liquid-pervious cover sheet with an aqueous emulsion incorporating an adhesive polymer, said coating printed in the form of a grid by means such as a gravure cylinder and thereby forming a coated underside;

removing the water from the emulsion thereby forming a residue of adhesive binder in the form of said grid on the underside of said cover sheet; and, contacting the coated underside of the cover sheet with the surface of the air-laid transport layer or surface of the absorbent core under sufficient pressure and an adhesive temperature not exceeding 105° C. to effect lamination of said coated underside of said cover sheet to the surface of said distribution layer or absorbent core.

There are numerous advantages associated with the disposable absorbent products and the methods for producing these disposable absorbent products and these include:

an ability to effect adhesion of the cover sheet to the distribution layer or absorbent core at discrete points over a substantially continuous area of contact surface;

an ability to effect an adhesive coating of the cover sheet without plugging of the perforations;

an ability to form discrete "perforated areas" within carded web cover sheets for enhanced transfer of fluids with simultaneous rewet retardation;

an ability to preform adhesively coating cover sheets onto large roll windings for storage for subsequent application to the nonwoven distribution layer;

an ability to eliminate the necessity of release sheets for adhesively coated, wound rolls of cover sheet, distribution layers or absorbent cores;

an ability to apply an adhesive to the underside of the cover sheet off-line thereby affording manufacturing flexibility;

an ability to apply the adhesive to the underside of the cover sheet via a print roller which reduces blockage of the pores and effect a more uniform application of the adhesive; and, an ability to reduce bubbling or puckering between the cover sheet and the transport layer or absorbent core;

DETAILED DESCRIPTION OF THE INVENTION

As used herein the term "absorbent article" refers to articles of manufacture which absorb and contain body exudates and those articles which are placed against or in proximity to the body of the wearer to absorb and contain these various exudates discharged from the body. Examples of disposable absorbent articles, disposable intended to refer to articles intended for discard after a single use, include such articles as training pants, diapers and liners and feminine hygiene garments such as sanitary napkins and panty liners.

Figure 1:
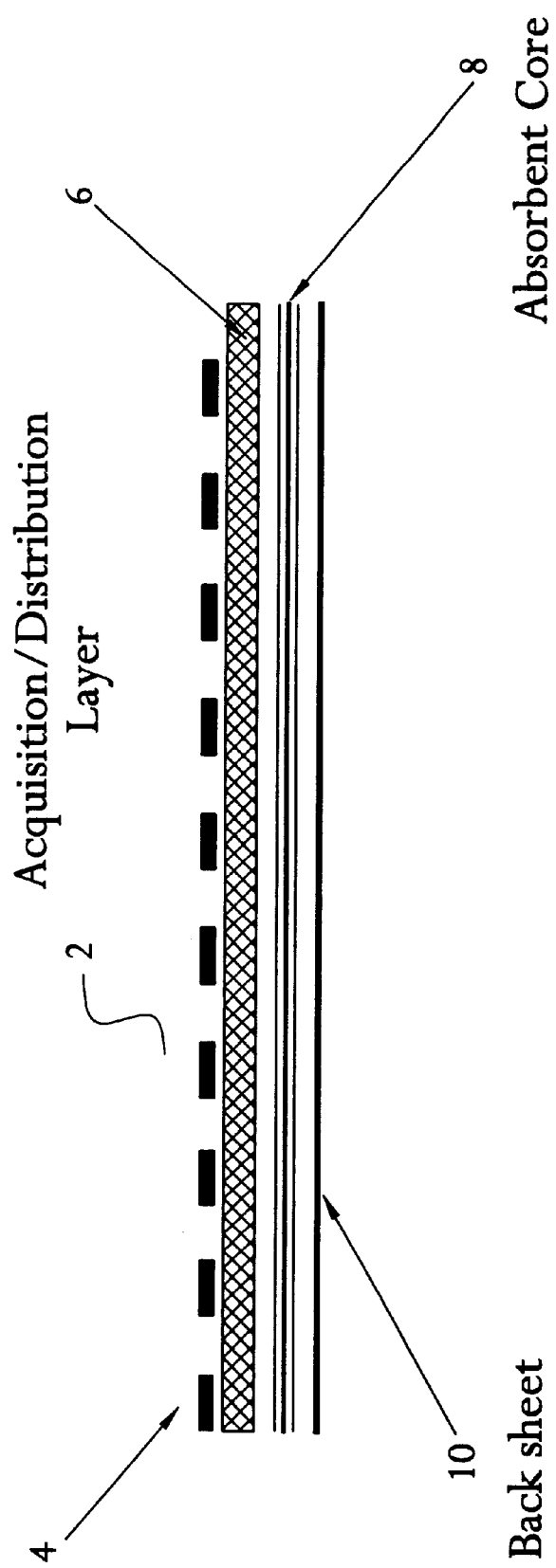
FIG. 1 is a cross-sectional view of an absorbent feminine pad illustrating the general components and structure.

For purposes of facilitating an understanding of the invention, reference is made to FIG. 1 which is a pictorial view of a feminine pad. The feminine pad 2 is comprised of a perforated cover sheet 4 to be placed in contact with the wearer, optionally a distribution or transfer layer 6, an absorbent core 8, a backsheet 10. Optionally, adhesive strips (not shown) often are attached to backsheet 10 for anchoring the pad to the wearer's garment.

Regarding the components of the disposable absorbent article, the cover sheet 4 should be compliant, soft feeling and non-irritating to the wearer's skin since it is either in contact or general proximate to the skin of the wearer. The cover sheet or top sheet is liquid pervious, permitting liquid or blood to penetrate through its thickness. Apertured plastic films and woven or nonwoven webs of natural and synthetic fibers are widely used in preparing the cover sheet. The cover sheet is generally made of a hydrophobic material to isolate the wearer's skin from liquids contained in the absorbent core and in some instances the structure of the absorbent core is adjusted to prevent fluids from migrating from the absorbent core back through the cover sheet and in contact with the wearer.

Cover sheets are usually made from polyethylene (PE) or polypropylene (PP) or a combination of the two or polyester fibers. Linear polyethylene has a glass transition of −80° C. and a melting temperature of 137° C. (279° F.). Polypropylene has a glass transition of −19° C. and a melting temperature of 176° C. (350° F.). Because the melt temperature of these two polymers is very sudden and there is a relatively sharp drop in the temperature profile from a solid state to a molten state, temperature control is important. Temperatures should not exceed 105° C. in order to minimized tearing, pinholing, etc.

Other forms of cover sheets may be used and these included carded fibrous webs. Common synthetic fibers used to form carded web cover sheets include polyesters, polypropylene and so forth may be used.

The transfer layer or distribution layer or fluid acquisition layer 6, as it is sometimes called, is disposed between the underside of the cover sheet and absorbent core and serves to quickly collect and temporarily hold discharged bodily fluids. A fluid, depending on the wearer's position, may be quickly transferred through the distribution layer and absorbed by the absorbent core 8 in the area of approximate discharge. If large quantities of fluid are discharged, the storage layer generally is not capable of absorbing the fluid as quickly as possible and thus the distribution layer also may facilitate transport of the fluid from the point of initial contact to other parts of the distribution layer and thus at different points to the absorbent core for storage. Another important feature of the distribution layer is its ability to permit greater utilization of the capacity of the absorbent core.

The distribution layer in unfolded configuration can be of many shapes which include rectangular, trapezoidal, oval, oblong, hourglass, etc. It may conform to the shape of the absorbent core but need not necessarily correspond to that general shape. Typically its surface will range from about 25 to 90% of the surface area of the storage layer but does not generally extend beyond the edge of the absorbent core at any boundary. It will have an average dry density of less than about 0.3 grams per centimeter cubed, sometimes less than 0.1 grams per centimeter cubed. One type of transfer distribution layer employed herein is formed by an air-laid process wherein a fibrous material is randomly distributed upon a belt and bonded with an emulsion polymerized adhesive binder. Another type of transfer layer is a polymeric foam, e.g., a polyurethane foam sprayed or coated with a thermoplastic adhesive binder of the type described herein for the absorbent core. As will be discussed, the adhesive binder employed is a key component in achieving superior results in the resulting laminate.

The absorbent core 8 in the disposable absorbent article generally is compressible, conformable and capable of absorbing and containing liquids such as urine, blood or other discharge exuded from the wearer. The absorbent core may be manufactured in a wide variety of sizes and shapes, e.g. rectangular, hour glass, "T" shape, asymmetric and they may be made from a variety of liquid-absorbent materials.

One of the common absorbent materials is a comminuted wood pulp generally referred to as air-felt. Other absorbent materials include crepe cellulose wadding, meltblown polymers including Coform, tissue including tissue wraps and tissue laminates, and hydrophilic polymers such as cellulosic fibers, rayon, polyester fibers which include polyethylene terephthalate, hydrophilic nylon as well as a mixture of hydrophobic polymers, e.g. surfactant-treated and silica-treated polyethylene and polypropylene, polyacrylics, polyamides, polystyrenes and so forth. In addition, current practice has been to incorporate super absorbent polymers and absorbent gelling materials into the absorbent core to enhance the absorbent capacity of the absorbent core.

The backsheet 10 is impervious to liquids, e.g., urine and blood and is preferably manufactured from a thin plastic film such as polyethylene or polypropylene or composite film-coated nonwoven material. The backsheet generally has a thickness of from about 0.5 to 2 mm. To provide a clothlike appearance, the backsheet, sometimes in combination with the other components of the absorbent article 2, may be embossed or matte finished and treated such that it may permit vapors to escape from the absorbent core while preventing exudates from passing through the backsheet to garments in contact with the backsheet. The backsheet 10 typically has tabs (not shown in FIG. 1) which have a pressure sensitive adhesive applied thereto for providing adhesive contact with the garment and thereby maintaining the article in place. Release papers generally are applied to the tabs for preventing sticking during storage; they are removed prior to application.

One of the more recent advances in compositional structure of the transfer layer 6 and absorbent core 8 is the incorporation of chemically stiffened cellulosic fibers to these components in an effort retard compaction under pressure. These chemically stiffened fibers tend to enhance fluid transfer through the transfer layer 6 and to promote enhanced absorption in absorbent core 8. As is well known a variety of stiffening agents such as $C_2$–$C_8$ dialdehydes and $C_2$–$C_9$ polycarboxylic acids have been widely used in the manufacture of such stiffened cellulosic fibers. These chemically stiffened fibers may be used in forming the absorbent cores herein.

Further information regarding materials employed in disposable absorbent articles, the construction of the disposable absorbent articles, their dimensions and method of manufacture are found in the patents described in the Background of the Invention. Specific US patents and publications showing most of these features include H1511, U.S. Pat. No. 5,533,991 and U.S. Pat. No. 4,690,679 and are incorporated by reference.

The key to establishing intimate contact between the underside of the cover sheet and the distribution layer not only resides in the method of applying the adhesive to the cover sheet but also to the emulsion polymers employed as an adhesive for the cover sheet and, in a preferred embodiment, the emulsion polymer employed for bonding the fibers in forming the air-laid nonwoven web either in the form of a transfer layer or absorbent core. The emulsion polymer used as an adhesive for the cover sheet is either a thermoplastic vinyl acetate or a $C_{1-8}$ alkyl ester of acrylic or methacrylic acid based adhesive or a combination of vinyl acetate and the $C_{1-8}$ alkyl ester of acrylic or methacrylic acid. The emulsion polymerized thermoplastic adhesive will have a Tg from −25 to 20° C., a solids content of from 45 to 60% by weight, typically from 52 to 60%, and a Brookfield viscosity (#4 spindle, 60 rpm at 20° C.) of from 5 to 1000 cps. In addition, the thermoplastic adhesive binder which is applied to the cover sheet and employed in bonding or coating the distribution layer or absorbent core should have an insoluble fraction in toluene at 20° C. of less than 45% and preferably less than 10% by weight. Adhesive binders having too high of an insoluble fraction, such as in thermoset binders, result in poorer laminate bonds. Preferred adhesives are vinyl acetate/ethylene based adhesives incorporating less than about 10%, and preferably less than 5% by weight, of a polymerized third monomer. Representative examples of third monomers which may be incorporated into the polymer include adhesion promoting monomers such as unsaturated carboxylic acid including acrylic and methacrylic acid, crotonic acid, and epoxide containing monomers such as glycidyl acrylate, glycidyl methacrylate and so forth. The emulsion polymerized vinyl acetate/ethylene polymers are stabilized employing a protective colloid or a combination of a protective colloid in surfactant as well as a surfactant. Preferably the surfactants are of the type that are one other than alkyl phenol ethoxylates.

The emulsion used in forming the distribution layer or used to bond the fibers in the air-laid nonwoven absorbent core is selected to be compatible with the thermoplastic adhesive employed for coating the cover sheet. By compatible, it is meant the adhesive should be thermoplastic. The corresponding thermoplastic vinyl acetate/ethylene and $C_1$–$C_8$ alkyl esters of acrylic and methyacrylic acid-based adhesives are employed for bonding the fibers in the transfer layer or absorbent core to those used as the adhesive applied to the cover sheet. Conventionally, it has been practice to employ crosslinkable binders (thermoset) in forming the nonwoven absorbent core to impart wet strength thereto. In the present case, it is preferred that the emulsion polymers be free from polymerized crosslinkable monomers, or if present, that the application temperatures and drying conditions are such that minimal crosslinking is effected in the nonwoven binder. The thermoset vinyl acetate/ethylene binders, such as vinyl acetate/ethylene having from 1–3% N-methylolacrylamide tend to be less flexible resulting in ply separation when attached to the thermoplastic adhesive coated cover sheet.

One type of distribution layer of absorbent core is made by a conventional air-laid technique wherein fibers are randomly placed on a belt and a polymeric latex sprayed onto the fibers and pulled through the fibers in order to enhance contact. The latex is applied to provide an add-on of polymer in an amount from about 10 to 30% by weight (dry) of the fibers or, in the alternative, from 1–20 preferably 4–8 grams per square meter. The other type of distribution layer is comprised of a thin polyurethane foam. When sprayed or contacted with the emulsion containing the adhesive binder, the polyurethane foam can be bonded to the cover sheet to form a laminate of exceptional quality.

One of the important components of the emulsion is the stabilizing system which is employed in the production of the aqueous emulsion, particularly in the production of vinyl acetate/ethylene emulsions. The stabilizing system affects overall effectiveness of the cover sheet bond. A variety of protective colloids and nonionic, anionic and cationic surfactants may be used to stabilize the emulsion while some are preferred. The level of protective colloid will range from 2 to 10%, generally 2–4% by weight of the monomers to be polymerized while the level of surfactant will range from 0.2 to 5%, generally from 0.2 to 5%, of the monomers to be polymerized.

Suitable non-ionic emulsifying agents include polyoxyethylene condensates. Polyoxyethylene condensates may be represented by the general formula:

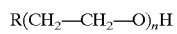
$$R(CH_2-CH_2-O)_nH$$

where R is the residue of a fatty alcohol containing 10–18 carbon atoms, an alkyl phenol, a fatty acid containing 10–18 carbon atoms, an amide, an amine, or a mercaptan, and where n is an integer of 1 or above. Some specific examples of polyoxyethylene condensates which can be used include polyoxyethylene aliphatic ethers such as polyoxyethylene lauryl ether, polyoxyethylene oleyl ether, polyoxyethylene hydroabietyl ether and the like; polyoxyethylene alkaryl ethers such as polyoxyethylene nonylphenyl ether, polyoxyethylene octylphenyl ether and the like; polyoxyethylene esters of higher fatty acids such as polyoxyethylene laurate, polyoxyethylene oleate and the like as well as condensates of ethylene oxide with resin acids and tall oil acids; polyoxyethylene amide and amine condensates such as N-polyoxyethylene lauramide, and N-lauryl-N-polyoxyethylene amine and the like; and polyoxyethylene thio-ethers such as polyoxyethylene n-dodecyl thio-ether.

One class of non-ionic emulsifying agents which can be used include a series of surface active agents known as "Pluronics." The "Pluronics" have the general formula:

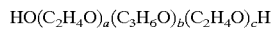
$$HO(C_2H_4O)_a(C_3H_6O)_b(C_2H_4O)_cH$$

where a, b, and c are integers of 1 or above. As b increases, the compounds become less water soluble or more oil soluble and thus more hydrophobic when a and c remain substantially constant.

Some examples of non-ionic emulsifying agents sold under the Pluronic trademark which can be used include polyoxyethylene-polyoxypropylene glycols conforming to the above general formula for "Pluronics" in which the polyoxypropylene chain has a molecular weight of 1500 to 1800 and the polyoxyethylene content is from 40 to 50 percent of the total weight of the molecule, a polyoxypropylene having a cloud point of about 140° F. and marketed under the trademark "Pluronic L-64,"; a polyoxyethylene-polyoxypropylene glycol conforming to the above general formula for "Pluronics" in which the polyoxypropylene chain has a molecular weight of 1500 to 1800 and the polyoxyethylene content is from 80 to 90 percent of the total weight of the molecule and having a cloud point of about 212° F. and marketed under the trade mark"Pluronic F-68.

"Pluronics" are obtained by condensing ethylene oxide on the polyoxypropylene base and the hydrophobic-hydrophilic nature of the resulting compound is controlled by varying the molecular weight of either the hydrophobic base or the hydrophilic portion of the molecule.

Another class of nonionic surfactants are sold under the Igepal trademark. One example within this class is a polyoxyethylene nonylphenyl ether having a cloud point of between 126 and 133° F. and marketed under the trade mark "Igepal CO-630"; another is polyoxyethylene nonylphenyl ether having a cloud point above 212° F. and marketed under the trade mark "Igepal CO-887." A similar polyoxyethylene nonylphenyl ether with a cloud point of about 86° F. is marketed under the trade mark "Igepal CO-610." Surfactants similar to the Igepal surfactants include a polyoxyethylene octylphenyl ether having a cloud point of between 80° F. and 160° F. marketed under the trademark "Triton X-100", a polyoxyethylene oleyl ether having a cloud point of between 80° F. and 160° F. marketed under the trade mark "Atlas G-3915" and a polyoxyethylene lauryl ether having a cloud point above 190° F. marketed under the trademark "Brij 35."

Of the surfactants, those of the Igepal surfactant type are preferred. These are free from phenolic ethoxylates which have been de-emphasized for these kinds of application because of regulatory reasons.

Protective colloids also can be used in combination with the above nonionic surfactants as a stabilizing agent. Representative colloids which can be used include polyvinyl alcohol, partially-acetylated polyvinyl alcohol, e.g., up to 50% acetylated, casein, hydroxyethyl starch, carboxymethylcellulose, gum arabic, and the like. Of these, hydroxyethyl cellulose is preferred.

Various free-radical forming catalysts such as peroxide compounds can be used in carrying out the emulsion polymerization of the monomers. Combination-type catalysts employing both reducing agents and oxidizing agents can also be used. Suitable reducing agents or activators include bisulfites, sulfoxylates, or other compounds having reducing properties such as ferrous salts, and tertiary aromatic amines, e.g., N,N-dimethylaniline. The oxidizing agents or initiators include hydrogen peroxide, organic peroxides such as benzoyl peroxide, t-butyl hydroperoxide and the like, persulfates, such as ammonium or potassium persulfate, perborates, and the like. A specific combination-type catalyst or redox system which can be used is hydrogen peroxide and sodium formaldehyde sulfoxylate.

The initiator is employed in the amount of 0.1 to 2%, preferably 0.25 to 0.75%, based on the weight of vinyl acetate introduced into the system. The activator is ordinarily added as an aqueous solution and the amount of activator is generally from 0.25 to 1 times the amount of initiator.

Figure 4:
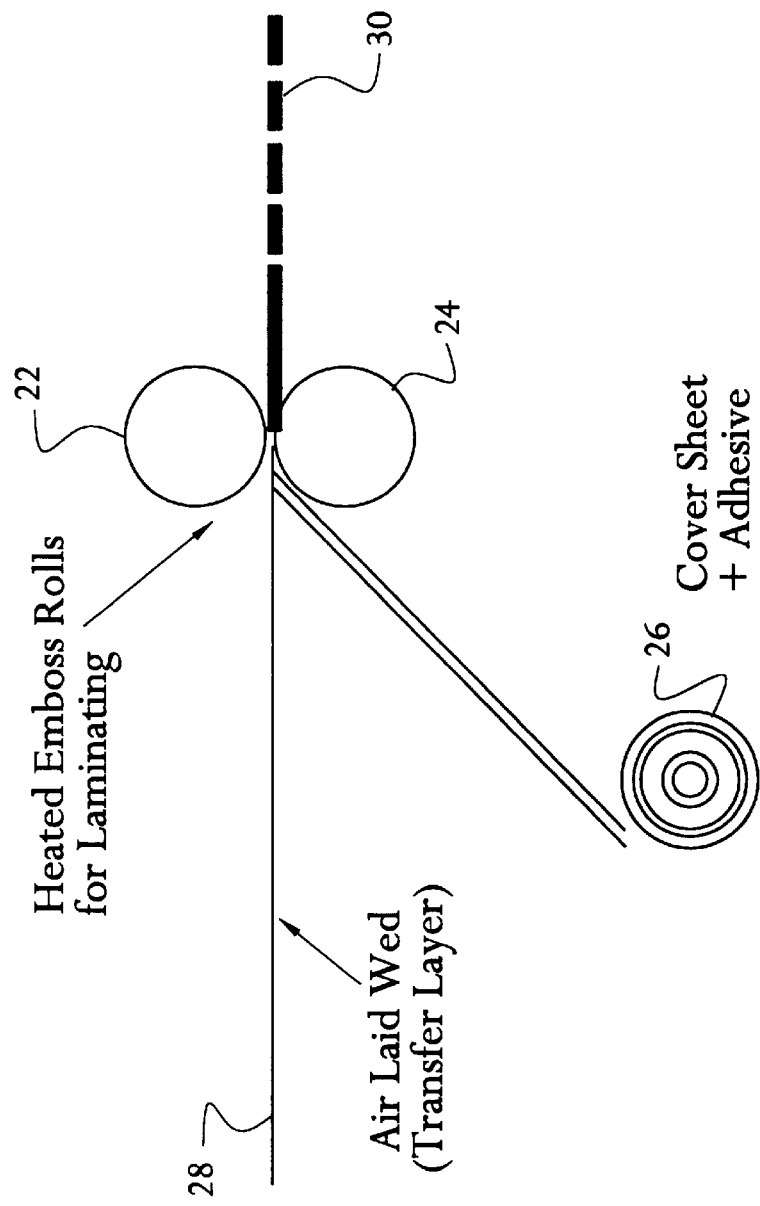
FIG. 4 is a side view of a representative mechanism for bonding or laminating the adhesive coated cover sheet to an air-laid distribution layer or adhesive coated polyurethane foam stock.

The emulsion polymerized thermoplastic polymeric adhesive is applied to the underside of the cover sheet in an amount of from 1 to 20 grams, preferably 4 to 8 grams, dry adhesive per square meter by a print method whereby a reticulated or grid pattern of adhesive (polygon) is coated onto the underside of the cover sheet. This grid pattern is generally continuous over the cover sheet to permit bond formation all along the surface. Recall that if the cover sheet were to separate from the transfer layer or absorbent core, as happens in bubbling or puckering of the cover sheet, liquid does not pass through the perforations, but is retained on the surface of the cover sheet thus causing irritation to the wearer. In printing a continuous sheet of perforated polyethylene or polypropylene the full surface may be printed with the emulsion. Because of the high solids and appropriate viscosity of the emulsion, the surface tension of the emulsion, at the application rate, causes the adhesive to remain substantially solely on the cover sheet without covering the perforations. In carded web cover sheets the sheet is printed via a gravure cylinder for producing an adhesive residue as a grid. A preferred print or grid pattern is a diamond shaped pattern as shown in FIG. 4 wherein the line width will range from 40 to 2000, preferably 10 to 20 microns, the line depth will range from 25 to 50 microns with the diamond long axis ranging from 500 to 1500 microns and the diamond short axis ranging from 250 to 750 microns. Both the perforated polyethylene or polypropylene cover sheets, as well as the carded web, may be printed using the gravure cylinder having a diamond pattern. Other patterns include 5 and six sided polygons.

Figure 2:
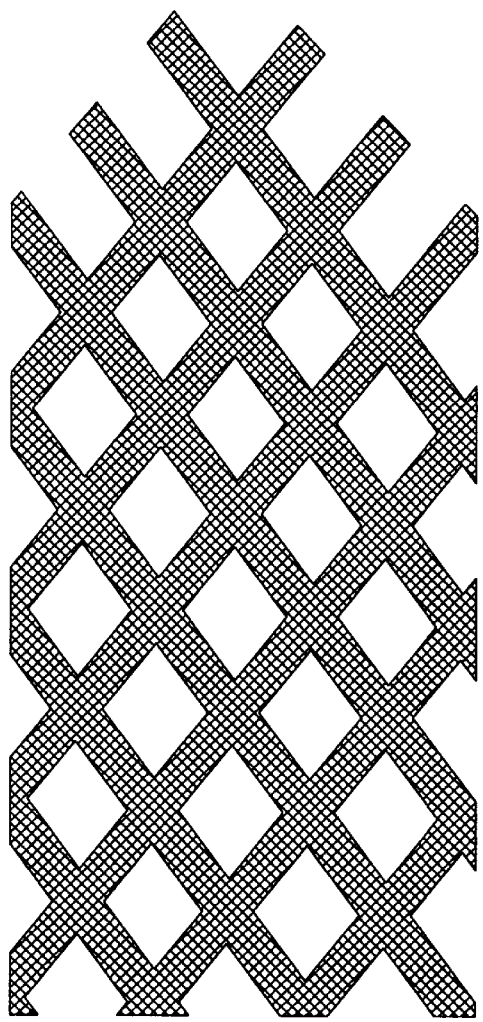
FIG. 2 is a view of a groove pattern on a gravure cylinder for depositing the emulsion onto cover sheets.

The higher solids level of the emulsion employed in print application (preferably 52 to 60% by weight of the emulsion) vis-a-vis spray methods which employ solids levels of from 4 to 30% by weight of the aqueous emulsion tends to coat only the solid areas in an apertured polyethylene film leaving the apertures open for transmission of body fluids through to the distribution layer or absorbent core. Also, when the print method is employed for applying the adhesive to a carded web cover sheet, the grid or reticulated pattern, such as the diamond pattern, generates in situ perforations within the cover sheet thus forming a cover sheet simulating perforated polyethylene and polypropylene. Body fluids are transferred therethrough but because of the relative hydrophobicity of the adhesive and the narrow dimensions of the adhesive grid pattern in the carded web, e.g., a diamond shaped pattern shown in FIG. 2, surface rewetting is reduced.

Figure 3:
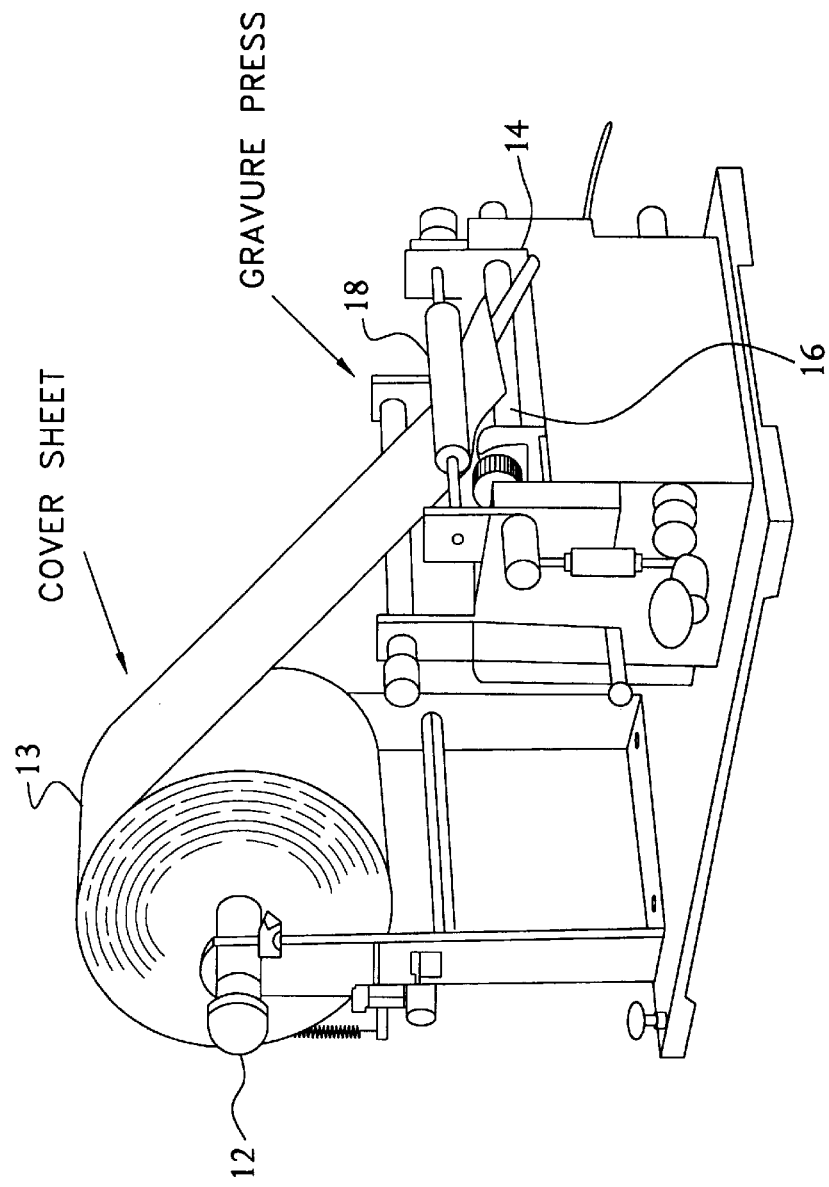
FIG. 3 is an isometric view of a Geiger press incorporating a gravure cylinder for applying an adhesive emulsion to wound cover stock.

FIG. 3 shows a Geiger press print coater for applying the adhesive to the cover sheet. More particularly, the print coater has mounting 12 for carrying a roll of uncoated cover stock 13, a tank 14 for holding adhesive, a gravure cylinder 16 with its under surface in contact with adhesive contained within tank 14. As gravure cylinder 16 rolls through and collects adhesive from tank 14, doctor blade (not shown) wipes off excess emulsion from the gravure cylinder to permit application of the adhesive emulsion in desired amount to the cover sheet. The cover sheet then is passed between gravure cylinder and roller wherein the adhesive is applied to the underside of the cover sheet. Roller 18 is used to maintain contact between the cover sheet and gravure cylinder 16 and thereby providing for continuous coating of the cover sheet. Subsequent to the application of the emulsion containing thermoplastic adhesive polymer to the cover sheet, the emulsion is dried at a temperature from (120° vs. 200° F.) and far below the deformation and distortion temperature of the polymeric materials employed in the cover sheet. Accordingly, any melting, pinholes, tears and the like in the cover sheet is eliminated or minimized by drying at such a low temperature.

FIG. 4 is a schematic of a roller mechanism for adhesively coating the cover sheet to the transfer layer or absorbent core. More particularly, the roller mechanism comprises a pair of rollers 22 and 24. The adhesively coated cover sheet 26 with its underside down is unwound for roll stock and contacted immediately prior to coming in contact with rollers 22 and 24 with the transfer layer 28. The transfer layer and cover sheet are pressed under rollers 22 and 24 to a roll pressure ranging anywhere from 10 to 20,000 psig at roll temperature typically from 200 to 300° F. for a period of from 0.5 to 3 second, generally from 1–2 seconds. The resulting laminate 30 is then wound onto a roller for subsequent conversion.

The following examples are provided to illustrate various embodiments of the invention and are not intended to restrict the scope thereof.

EXAMPLE 1

Effect of Adhesive Coat on Peel Strength Between Cover Sheet and Transport Layer To prepare samples for testing, the cover sheets coated with the adhesive were cut into two inch strips and sealed to an air laid base sheet of the type typically used in the absorbent product as a transport layer or absorbent core (FIG. 4). The air laid web had been bonded with a non-woven binder designated JVH at an application rate of 20% add-on based on the dry weight of the fiber. A "Sen-Tinel Heat Sealer" was used to form a bond between the cover sheet and the air-laid web. A pressure used to form the bond between the two plies was kept constant at 60 psig.

The emulsions were applied to a carded web cover sheet by means of a grooved gravure cylinder having grooves in the form of a diamond shaped pattern. The solids content of the emulsions ranged from 52 to 56% by weight of the emulsion. The weight of solid adhesive polymer added to the cover sheet varied from about 4 to 8 grams/m$^2$. After the emulsion had been applied, the water was removed via drying at elevated temperatures. If a crosslinking monomer had been incorporated into the emulsion, then conditions were controlled to effect desired crosslinking. The resulting carded web had an adhesive residue in the form of a diamond shaped grid.

Test samples were evaluated for peel strength which is the force required to peel apart the different layers of the bonded product, i.e., the cover sheet from the transfer layer. To check the effect of temperature and dwell time on peel strength, a test known in industry as the "T-peel" test was employed. An instrument manufactured by Instron was used to measure the force required to pull the bonded layers apart. This test comprised clamping the unbonded portion of the composite structure in two claming jaws of the instrument and then pulling the layers apart. The force required to pull or peel the two plies of the composite apart was recorded as the peel strength. Table 1 sets forth the results and Table 2 sets forth measured approximate adhesive temperatures based upon the temperature of the gravure cylinder roll and the dwell time.

TABLE 1

| Binder | Sen-Tinel Temp. Set Deg F. | Peel 0.1 sec g/1" | Strength 0.5 sec g/1" | After 1 sec g/1" | Time 3 sec g/1" |
|---|---|---|---|---|---|
| JVH | 250 | 0 | 33 | 88 | 244 |
|  | 300 | 0 | 38 | 111 | 384 |
|  | 350 | 0 | 39 | 128 | 404 |
| 2 | 250 | 0 | 0 | 24 | 77 |
|  | 300 | 0 | 0 | 74 | 215 |
|  | 350 | 0 | 0 | 78 | 244 |
| 3 | 250 | 0 | 0 | 36 | 111 |
|  | 300 | 0 | 20 | 77 | 259 |
|  | 350 | 0 | 51 | 117 | 307 |
| 4 Cured | 250 | 0 | 0 | 0 | 0 |
|  | 300 | 0 | 0 | 0 | 0 |
|  | 350 | 0 | 0 | 0 | 163 |
| 5 Cured | 250 | 0 | 0 | 0 | 44 |
|  | 300 | 0 | 0 | 0 | 77 |
|  | 350 | 0 | 0 | 0 | 162 |

TABLE 1-continued

| Binder | Sen-Tinel Temp. Set Deg F. | Peel 0.1 sec g/1" | Strength 0.5 sec g/1" | After 1 sec g/1" | Time 3 sec g/1" |
|---|---|---|---|---|---|

Adhesive JVH was a vinyl acetate/ethylene adhesive having a Tg of +3° C. stabilized with hydroxyethyl cellulose and surfactant, a Brookfield viscosity #4 spindle, 60 rpm of 184 cps. The toluene insoluble fraction was estimated to be less 10% by weight.
Adhesive 2 was a vinyl acetate/ethylene polymer having a Tg of −24° C., polyvinyl alcohol stabilized, a viscosity of 340 cps. The toluene insoluble fraction was estimated to be from 30 to 40% by weight.
Adhesive 3 was a vinyl acetate/ethylene polymer having a Tg of 0° C., poly(vinyl alcohol) stabilized, a viscosity of 1224 cps. The toluene insoluble fraction was estimated to be less 10% by weight.
Adhesive 4 was a vinyl acetate/ethylene/3% N-methylolacrylamide polymer having a Tg of −15, surfactant stabilized, a viscosity of 274 cps. The toluene insoluble fraction was estimated to be greater than 45% by weight.
Adhesive 5 was a vinyl acetate/ethylene/ 3% N-methylolacrylamide polymer having a Tg of 0° C., surfactant stabilized, a viscosity of 316 cps. The toluene insoluble fraction was estimated to be greater than 45% by weight.

TABLE 2

| Set Temp Deg F. | Dwell Time Sec. | Observed Temp Deg C. | Observed Temp Deg F. |
|---|---|---|---|
| 250 | 0.1 | 29.0 | 52.2 |
|  | 0.5 | 37.0 | 66.6 |
|  | 1.0 | 67.0 | 120.6 |
|  | 3.0 | 71.0 | 127.8 |
| 300 | 0.1 | 31.8 | 57.2 |
|  | 0.5 | 57.2 | 103.0 |
|  | 1.0 | 71.4 | 128.5 |
|  | 3.0 | 98.9 | 178.0 |
| 350 | 0.1 | 37.0 | 66.6 |
|  | 0.5 | 70.2 | 126.4 |
|  | 1.0 | 74.0 | 133.2 |
|  | 3.0 | 102.0 | 183.6 |

The results in Table 1 show that the best results in terms of peel strength, particularly at low temperatures, (250–300° F. roll temperatures) were obtained by the JVH adhesive. It was stabilized with hydroxyethyl cellulose and surfactant and had a low toluene insoluble fraction. Poorer results were obtained with the polyvinyl alcohol stabilized adhesive (Adhesive 3). It is speculated that the higher toluene insoluble fraction and reduced plasticity to that of the JVH emulsions contributed to the reduced results. However, the results were adequate. The results of adhesives 4 and 5 indicate that the "thermoset" crosslinked binder employed in the transport layer to enhance wet strength should not be used where good peel strength is required. Adhesion is effected only at the higher temperatures (roll temp 350° F. for 3 seconds. Actual temperatures approached the melting point temperatures of the polymers used to form the cover sheet as noted in Table 2 and that fact alone probably contributed to the adhesion. Therefore, these emulsions should not be used when preferred peel strengths are required.

EXAMPLE 2

Effect of Adhesive Coat on Cover Sheet Absorbency Rate and Absorbent Capacity General Procedure Two different carded cover sheets were prepared for testing in combination with an absorbent core bonded with the JVH adhesive. One of the cover sheets was made from 100% polypropylene fibers and the second was comprised of a combination of polypropylene and polyethylene fibers. A "Geiger" press and gravure cylinder for providing pattern was used to apply the emulsion based self sealable binder to the underside of the cover sheets. The JVH binder was applied at a rate of 4 to 8 grams of binder per square meter of the cover sheet. The print fluid viscosity of the emulsion was formulated to consist of 52% solids and varied from 180 to 1230 cps without addition of any wetting agents. Water was removed from the emulsion by means of a heat gun blowing a stream of hot air at temperature of about 120° F. onto the surface of the coated cover sheet. This temperature was high enough to dry the emulsion but not enough to cure those binders having the N-methylol acrylamide cross linking agent. Table 3 sets forth the results obtained for absorbency rate and absorbency capacity.

TABLE 3

| SAMPLE ID | Basis wt g/m2 | A"JVH" Binder on Cover g/m2 | Wet Bulk cc/g | Absorbency Capacity g/g | Absorbency Rate g/g/s |
|---|---|---|---|---|---|
| Control | 127 | 0 | 8.1 | 6.6 | 0.4 |
| PP/PE Cover with JVH web | 133 | 6 | 7.2 | 5.8 | 0.4 |
| PP Cover/JVH web | 107 | 0 | 7.6 | 6.9 | 0.6 |
|  | 113 | 6 | 7.3 | 6.6 | 0.5 |

These results show that the webs coated with the JVH adhesive were not affected in terms of its absorbent capacity and absorbency rate in relation to the control cover sheets. That is a favorable result because it shows that the extensive adhesive bond pattern did not affect the permeation properties of the cover sheet.

EXAMPLE 3

Effect of Print vs. Spray Application on Absorbency Rate and Absorbent Capacity The purpose of this example was to determine the effectiveness of spray application verses print in terms of absorbency rate and capacity. The components employed were essentially the same as in Example 2. In spray application, the viscosity of the JVH binder had to be lowered to about 10 cps from that employed in Example 2. The lower viscosity product was used because the emulsions atomized better. The viscosity was reduced by lowering the percent solids of a vinyl acetate/ethylene (VAE) type binder from 52 percent to about 20 percent solids. This resulted in a typical viscosity value of 4 cps depending on the original viscosity of the emulsion.

Table 4 shows the difference in absorbency rate between the printed product as compared to the cover sheet which was sprayed with the same emulsion.

TABLE 4

Effect of Application Method on Peel Strength & Absorbency

| Application Method | B.W. g/m2 | Abs. g/g | Rate g/g/s | Peel Str.* g/5cm |
|---|---|---|---|---|
| Control | 86 | 9.6 | 0.59 | NA |
| Print (A-410) | 98 | 8.9 | 0.64 | 495 |
| Spray (A-410) | 97 | 6.5 | 0.37 | 563 |

Note: Samples were bonded at 150 F. using press at 10 tons of pressure and 8 sec.

The results in Table 4 show that the laminated products formed by the print process had higher absorbency rates and higher absorbent capacities than did those formed by the spray process. It is speculated that the spray method of application to form an adhesive coated carded cover sheet rather than the print method resulted in indiscriminate coverage whereas the printed diamond shaped pattern formed small apertures to permit fluid transfer to the absorbent core.

EXAMPLE 4

The procedure of Example 3 was repeated except that a perforated polyethylene cover sheet was employed, i.e., the third cover sheet was a commercial apertured polyethylene film. The spray method of forming the adhesive coated cover sheet was inferior to that of the printed method of Example 1.

EXAMPLE 5

Adhesive Effect of Binder in Nonwoven Web On Adhesion to That Applied to the Cover Sheet The procedure of Example 1 was repeated except the binder used to form the nonwoven web was varied as indicated in Table 5 thus replacing the JVH binder. The JVH binder was used to bond the cover sheet to the transport layer. The results are set forth in Tables 5.

TABLE 5

| Product | Binder | Sen-Tinel Temp. Set Deg F. | Peel Strength after 3 sec g/1" |
|---|---|---|---|
| Air Laid | JVH1 | 150 | 64 |
|  |  | 250 | 160 |
|  |  | 350 | 196 |
| Air Laid | 2 | 150 | 0 |
|  |  | 250 | 10 |
|  |  | 350 | 17 |
| Air Laid | 3 | 150 | 54 |
|  |  | 250 | 122 |
|  |  | 350 | 139 |
| Air Laid | Cured4 | 150 | 0 |
|  |  | 250 | 0 |
|  |  | 350 | 0 |
| Air Laid | Cured5 | 150 | 0 |
|  |  | 250 | 0 |
|  |  | 350 | 0 |

Adhesive JVH was a vinyl acetate/ethylene adhesive having a Tg of +3° C. stabilized with hydroxyethyl cellulose and surfactant, a Brookfield viscosity #4 spindle, 60 rpm of 184 cps. The toluene insoluble fraction was estimated to be less 10% by weight.
Adhesive 2 was a vinyl acetate/ethylene polymer having a Tg of −24° C., polyvinyl alcohol stabilized, a viscosity of 340 cps. The toluene insoluble fraction was estimated to be from 30 to 40% by weight.
Adhesive 3 was a vinyl acetate/ethylene polymer having a Tg of 0° C., surfactant stabilized, a viscosity of 1224 cps. The toluene insoluble fraction was estimated to be less 10% by weight.
Adhesive 4 was a vinyl acetate/ethylene/3% N-methylolacrylamide polymer having a Tg of −15, surfactant stabilized, a viscosity of 274 cps. The toluene insoluble fraction was estimated to be greater than 45% by weight.
Adhesive 5 was a vinyl acetate/ethylene/ 3% N-methylolacrylamide polymer having a Tg of 0° C., surfactant stabilized, a viscosity of 316 cps. The toluene insoluble fraction was estimated to be greater than 45% by weight.

It was observed that the bond strength was very low when a fully cured air-laid web containing a self crosslinkable binder was used in place of the thermoplastic JVH binder. It is believed one of the reasons for poor adhesion is that the thermoset binders (Adhesives 4 and 5) offered very little chance for the binder to flow at low temperature. The only bond strength, which was observed at the longer dwell time and temperature, was due to the flow of the adhesive (A-JVH) printed on the cover sheet. The runs 2 and 3 binders did not contain any self cross-linking agents and they formed better bonds at the lowest temperatures. This could be attributed to the ability of the thermoplastic adhesive emulsion to flow at low temperature and form the desired bond. A suggested reason for improved results with the JVH binder is that the stabilizer is hydroxyethyl cellulose and the adhesive was more thermoplastic. The adhesives in runs 2 and 3 were stabilized with poly(vinyl alcohol) and surfactant.

EXAMPLE 6

Effect of Employing Pressure Sensitive Adhesive

The procedure of Example 1 was repeated except that a pressure sensitive adhesive was substituted for the JVH adhesive. A Sentinel Heat Sealer was used at a pressure of 60 PSIG. Table 6 sets forth the results.

TABLE 6

| Sen-Tinel Temp. Set Deg F. | 1 sec gr/1 in | Peel Strength after 5 sec gr/1 in | 1 sec gr/1 in | 3 sec gr/1 in |
| --- | --- | --- | --- | --- |
| 150 | 10 | 32 | 45 | 75 |
| 250 | 9 | 58 | 87 | 141 |

The results in Table 6 show that there is insignificant peel bond strength when laminate with the pressure sensitive adhesive was effected at low temperatures compared to the JVH binder employed in Example 1. There is an additional problem with the use of pressure sensitive adhesives (bonds on finger tip pressure) and that is one of migration. When the cover sheets are wound on a roll, some of the pressure sensitive adhesive may migrate to the backside of the cover sheet and thus, when worn, the pressure sensitive adhesive may come in contact with the wearer.

EXAMPLE 7

Transfer Layer of Polyurethane Foam

The procedure of Example 1 was repeated except that a polyurethane foam having a thickness of about 1/16 of an inch was used as the distribution layer. The polyurethane foam was sprayed with a the JVH emulsion binder at an application rate of from about 4–8 grams/M$^2$ (dry polymer) and the water removed by drying. The coated cover sheet and adhesive sprayed transfer layer were pressed between embossing rolls and the laminate was evaluated for peel strength. A finger peel test suggested a good bond between the cover sheet and the polyurethane distribution layer. When the cover sheet was contacted with droplets of water, the water quickly penetrated the cover sheet and was transferred to the absorbent core. Within matter of seconds the surface of the laminate was dry to the touch, the liquid being transferred to the absorbent core. Untreated polyurethane foam does not bond readily to the cover sheet and liquid is retained on the surface of the cover sheet.

What is claimed is:

1. In a disposable absorbent article such as a sanitary napkin, etc. having multi-layer construction comprised of a liquid permeable cover sheet having a wearer contact side and an underside, optionally an air-laid nonwoven distribution or transfer layer, at least one air-laid nonwoven absorbent core and a liquid-impermeable backsheet, the disposable absorbent article constructed such that said absorbent core is disposed between the cover sheet and said backsheet and said distribution layer disposed between the underside of said cover sheet and said absorbent core, the improvement in the disposable absorbent article which resides in an improved bond for providing generally continuous contact between the cover sheet and said distribution layer or said absorbent core and comprised of the following:

said liquid-pervious cover sheet having said underside coated with a thermoplastic adhesive binder obtained by emulsion polymerization, said thermoplastic adhesive binder applied via a print roller to its underside and forming a substantially continuous adhesive grid pattern on the underside of said cover sheet;

said distribution layer or absorbent core each formed from an air-laid, nonwoven web comprised of randomly distributed fibers or polymeric foam, the distribution layer or absorbent core bonded with a binder obtained by emulsion polymerization, said binder employed in forming distribution layer or absorbent core being adhesively compatible with said binder bonded to the adhesive on said cover sheet; and, said underside of said liquid-pervious cover sheet coated with an adhesive binder and bonded to the surface of the distribution layer or absorbent core.

2. The disposable absorbent article of claim 1 wherein the adhesive is applied on the underside of the cover sheet in an amount of from 1–20 grams/M$^2$.

3. The disposable absorbent article of claim 2 wherein the Tg of the adhesive is from −25 to 20° C. and the percent of the thermoplastic adhesive binder which is insoluble in toluene at 25° c is less than 45% by weight.

4. The disposable absorbent article of claim 3 wherein emulsion has a Brookfield viscosity of from 5 to 1000 centipoises as measured by a number 4 spindle at 60 rpm and 25° C.

5. The disposable absorbent article of claim 2 wherein the adhesive applied to the cover sheet is comprised of vinyl acetate and ethylene and has less than 10% by weight of polymerized third monomer.

6. The disposable absorbent article of claim 5 wherein the emulsion applied to the cover sheet is stabilized by hydroxyethyl cellulose and surfactant.

7. The disposable absorbent article of claim 6 wherein the emulsion containing the thermoplastic adhesive binder applied to the distribution layer or present in the absorbent core is comprised of vinyl acetate and ethylene and has less than 10% by weight of polymerized third monomer.

8. The disposable absorbent article of claim 7 wherein adhesive applied to the distribution layer or absorbent core in an amount of from 5 to 30% by weight on a dry basis.

9. The disposable absorbent article of claim 7 wherein the cover sheet is a carded web and the adhesive binder printed onto the surface of the cover sheet is in the form of a diamond shaped pattern.

10. The disposable absorbent article of claim 7 wherein the cover sheet is perforated polyethylene of polypropylene.

11. The disposable absorbent article of claim 7 wherein the percent solids of the emulsion printed on the cover sheet is from 52 to 60% by weight and the percent insoluble in toluene at 25° C. is less than 10% by weight.

12. In a process for bonding a cover sheet to a transfer layer or absorbent core for incorporation into a disposable absorbent article such as a sanitary napkin, having multi-layer construction, the disposable absorbent article comprised of a liquid permeable cover sheet having a wearer contact side and an underside, a distribution or transfer layer, at least one absorbent core and a liquid-impermeable backsheet, the disposable absorbent article constructed such that the absorbent core is disposed between the cover sheet and the back sheet and the distribution layer disposed between the underside of the cover sheet and the absorbent core, the improvement for providing an improved bond for effecting generally continuous contact between the cover sheet and transfer layer or absorbent core comprises:

coating the underside of the liquid-pervious cover sheet with an aqueous emulsion incorporating an adhesive polymer, said coating being applied in the form of a grid thereby forming a coated underside;

removing the water from the emulsion thereby forming a grid residue of adhesive binder on the underside of said cover sheet; and, contacting the coated underside of the cover sheet with the surface of the transport layer or surface of the absorbent core and applying sufficient pressure and a temperature not exceeding 105° C. to effect lamination of said coated underside of said cover sheet to the surface of said distribution layer or said absorbent core.

13. The process for forming the disposable absorbent article of claim 1 wherein the adhesive is applied to the underside of the cover sheet in an amount of from 1–20 grams/m².

14. The process for forming the disposable absorbent article of claim 13 wherein the Tg of the adhesive is form −25 to 20° C.

15. The process for forming the disposable absorbent article of claim 14 wherein the absorbent core is an air-laid nonwoven web.

16. The process for forming the disposable absorbent article of claim 13 wherein the adhesive is comprised of vinyl acetate and ethylene and has less than 10% by weight of polymerized third monomer.

17. The process for forming the disposable absorbent article of claim 16 wherein the emulsion applied to the cover sheet is stabilized by hydroxyethyl cellulose and surfactant.

18. The process for forming the disposable absorbent article of claim 17 wherein the emulsion containing the adhesive binder applied to the distribution layer or air-laid absorbent core is comprised of vinyl acetate and ethylene and has less than 10% by weight of polymerized third monomer.

19. The process for forming the disposable absorbent article of claim 18 wherein the adhesive is applied to said underside of said cover sheet by means of a gravure cylinder.

20. The process for forming the disposable absorbent article of claim 19 wherein the gravure cylinder is grooved such that the grooves are in the form of a diamond shaped pattern.

21. The process for forming the disposable absorbent article of claim 16 wherein the adhesive is applied to the distribution layer or absorbent core in an amount of from 5 to 30% by weight on a dry basis.

22. The process for forming the disposable absorbent article of claim 21 wherein the cover sheet and distribution layer or absorbent core are passed between rollers heated to a temperature of from 200 to 300° F. for a period of from 0.5 to 3 seconds.

23. The process for forming the disposable absorbent article of claim 21 wherein the distribution layer is a polyurethane foam.

* * * * *